(12) United States Patent
Al-Tawil

(10) Patent No.: US 8,579,766 B2
(45) Date of Patent: Nov. 12, 2013

(54) HEAD SET FOR LINGUAL MANIPULATION OF AN OBJECT, AND METHOD FOR MOVING A CURSOR ON A DISPLAY

(76) Inventor: Youhanna Al-Tawil, Knoxville, TN (US)

( * ) Notice: Subject to any disclaimer, the term of this patent is extended or adjusted under 35 U.S.C. 154(b) by 369 days.

(21) Appl. No.: 13/092,234

(22) Filed: Apr. 22, 2011

(65) Prior Publication Data

US 2011/0287392 A1 Nov. 24, 2011

Related U.S. Application Data

(63) Continuation-in-part of application No. 12/782,356, filed on May 18, 2010, now Pat. No. 8,047,964, which is a continuation-in-part of application No. 12/556,237, filed on Sep. 9, 2009, now Pat. No. 7,942,782.

(60) Provisional application No. 61/096,408, filed on Sep. 12, 2008.

(51) Int. Cl.
*A63B 24/00* (2006.01)
(52) U.S. Cl.
USPC ................. 482/1; 482/11; 600/587; 600/590
(58) Field of Classification Search
USPC ............................ 482/1–11, 900–902; 701/1; 600/587–590, 23; 434/185, 247
See application file for complete search history.

(56) References Cited

U.S. PATENT DOCUMENTS

| 4,408,192 A | 10/1983 | Ward et al. |
| 4,562,432 A | 12/1985 | Sremac |
| 4,567,479 A | 1/1986 | Boyd |
| 4,629,424 A | 12/1986 | Lauks et al. |
| 4,697,601 A | 10/1987 | Durkee et al. |
| 4,746,913 A | 5/1988 | Volta |
| 4,758,829 A | 7/1988 | Smith |
| 4,865,610 A * | 9/1989 | Muller ............................ 623/24 |

(Continued)

OTHER PUBLICATIONS

Y. Takahashi, et al., High-speed Pressure Sensor Grid for Humanoid Robot Foot, IEEE/IROS (2005).

(Continued)

*Primary Examiner* — Glenn Richman
(74) *Attorney, Agent, or Firm* — Peter L. Brewer; Baker Donelson

(57) ABSTRACT

A head set is provided. The head set is beneficial for assisting an individual who is significantly impaired in the use of his or her upper extremities. The system enables this individual to manipulate an object through lingual movement. The object may be a mechanical device such as a door or a bed. Alternatively, the object may be an appliance, wherein "moving" the appliance means turning it on, off, up or down. Alternatively still, the object may be a cursor on a digital display or screen that facilitates the typing of alphanumeric characters on a virtual keyboard. The head set includes a head piece. The head piece supports an articulating arm. The articulating arm supports a mouthpiece at a distal end. The mouthpiece has a plurality of cells embedded therein. The cells are configured to receive pressure applied by the tongue of the user. Movement of the tongue over and against the cells causes the object to be moved, either directly or through a cursor on a display. A method for moving an object using a mouthpiece controlled through lingual movement is also provided. In addition, a method of typing characters on a virtual keyboard using lingual musculature is offered.

60 Claims, 7 Drawing Sheets

(56) References Cited

U.S. PATENT DOCUMENTS

| | | | |
|---|---|---|---|
| 5,212,476 A | | 5/1993 | Maloney |
| 5,422,640 A | | 6/1995 | Haley |
| 5,452,727 A | | 9/1995 | Tura et al. |
| 5,460,186 A | * | 10/1995 | Buchhold ............ 600/590 |
| 5,523,745 A | | 6/1996 | Fortune et al. |
| 5,609,161 A | | 3/1997 | Tura et al. |
| 5,689,246 A | | 11/1997 | Dordick et al. |
| 5,830,235 A | | 11/1998 | Standley |
| 5,904,140 A | | 5/1999 | McGoogan |
| 5,954,673 A | | 9/1999 | Staehlin et al. |
| 6,033,367 A | | 3/2000 | Goldfield |
| 6,108,592 A | | 8/2000 | Kurtzberg et al. |
| 6,190,335 B1 | | 2/2001 | Howard et al. |
| 6,430,450 B1 | | 8/2002 | Bach-y-Rita et al. |
| 6,511,441 B1 | | 1/2003 | Wakumoto et al. |
| 6,702,765 B2 | | 3/2004 | Robbins et al. |
| 6,893,406 B2 | | 5/2005 | Takeuchi et al. |
| 6,897,788 B2 | | 5/2005 | Khair et al. |
| 6,971,993 B2 | | 12/2005 | Fletcher |
| 7,127,270 B2 | * | 10/2006 | Sinclair ............ 455/556.1 |

OTHER PUBLICATIONS

Pressure Mapping Systems article, http://www.sensorland.com/HowPage033.html (May 22, 2008) (7 pages).

Pressure Transducers article, http://www.omega.com/prodinfo/pressuretransducers.html (May 27, 2008) (3 pages).

Piezoelectric sensor article, http://en.wikipedia.org/wiki/Piezoelectric_sensor (May 27, 2008) (5 pages).

ASDX Sensors brochure, www.honeywell.com/sensing (Sep. 28, 2009) (4 pages).

Adult Pacifier article, http://www.diaperconnection.com/pacifier.html (Sep. 28, 2009) (3 pages).

* cited by examiner

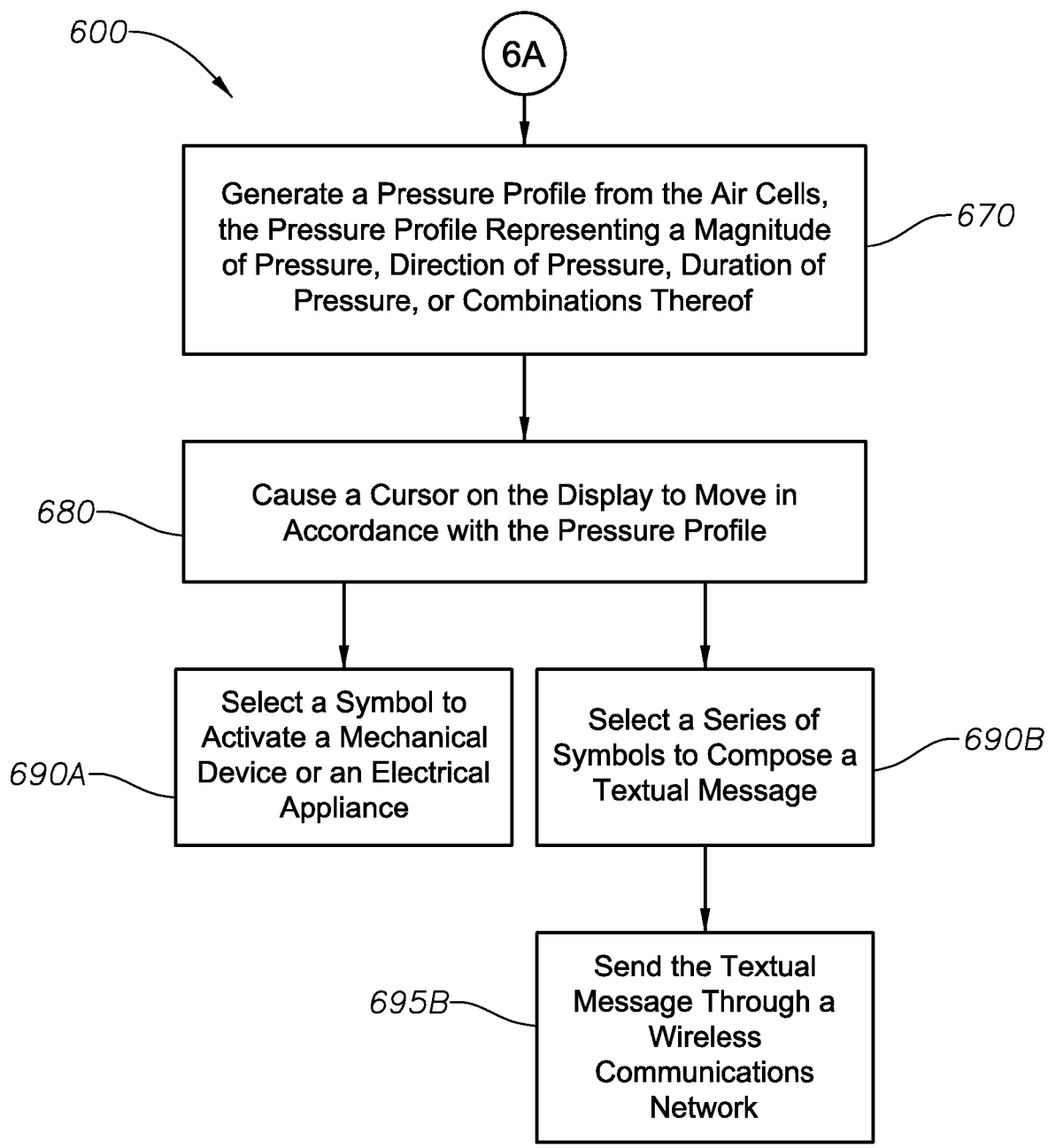

HEAD SET FOR LINGUAL MANIPULATION OF AN OBJECT, AND METHOD FOR MOVING A CURSOR ON A DISPLAY

CROSS REFERENCE TO RELATED APPLICATIONS

This application claims the benefit and is a continuation-in-part of a non-provisional patent application, U.S. Ser. No. 12/782,356, filed May 18, 2010. That application is entitled "Methods and Systems for Lingual Movement to Manipulate an Object." That application issued in November of 2011 as U.S. Pat. No. 8,047,964.

The non-provisional application claimed the benefit and was a continuation-in-part of U.S. Ser. No. 12/556,237, filed Sep. 9, 2009. That application is also entitled "Methods and Systems for Lingual Movement to Manipulate an Object." The '237 non-provisional patent application claimed the benefit of a provisional patent application bearing U.S. Ser. No. 61/096,408, filed Sep. 12, 2008.

These prior applications are incorporated herein by reference in their entireties.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

BACKGROUND OF THE INVENTION

1. Field of the Invention

The present invention relates to head sets. More specifically, the present invention relates to a head set that allows an individual who has limited use of their upper extremities to change the position or status of an object through lingual manipulation. The invention also relates to communication devices.

2. Technology in the Field of the Invention

Some individuals have limited use of their upper extremities. Such individuals may, for example, have suffered a stroke. The term "stroke" is a lay term that refers to a condition wherein the blood supply to an area of the brain is temporarily cut off. When blood fails to get through to parts of the brain, the oxygen supply to those areas is cut off. Without oxygen, brain cells die. The longer the brain is without blood, the more severe the damage will be. Where the portion of the brain that controls movement of the upper extremities is damaged, the individual may be left in a state of paralysis.

Sometimes individuals may lose function of their upper extremities as a result of an injury. Such injuries may occur due to a car accident, a diving accident, a fall, or other trauma. In these instances, the individual's cervical spine and nerves may be injured, producing partial or complete paralysis of the hands or arms.

In addition to these events, some individuals may develop paralysis as a result of a medical condition. Examples of such conditions include amyotrophic lateral sclerosis (ALS), hypokalemic periodic paralysis, or other diseases. Finally, some individuals may completely lose all or a portion of both arms due to an explosion or accident incident to military duty.

When any of these conditions of paralysis or injury occur, the individual is left without the ability to move an object using his or her arms. Thus, the individual cannot turn off a light, adjust a bed, change a channel, send text messages, or countless other activities that most people take for granted.

Therefore, a need exists for an apparatus that will allow an individual having limited use of their upper extremities to move an object. Further, a need exists for a head set having a connected mouthpiece that allows an individual to move a cursor or other object using lingual manipulation. Finally, a need exists for a head set that enables the typing of characters on a digital keyboard for the purpose of sending a text message.

BRIEF SUMMARY OF THE INVENTION

A head set is first provided herein. The head set is beneficial for assisting an individual who is significantly impaired in the use of his or her upper extremities. The system enables such an individual to manipulate an object. The object may be a mechanical device such as a door or a bed. Alternatively, the object may be an appliance, wherein "moving" the appliance means turning it on, off, up or down. Alternatively still, the object may be a cursor on a digital display or screen.

In one embodiment, the head set first includes a head piece. The head piece preferably comprises a pair of opposing head rests joined together by an arched support member. At least one of the head rests is adjustable relative to the support member.

The head set also includes an articulating arm. The articulating arm extends from the head piece, and has a distal end. In one aspect, the articulating arm comprises a first arm portion extending from one of the head rests, and a pivot point away from the head rest. The articulating arm then comprises a second arm portion connected to the pivot point, and having the distal end of the arm extending away from the pivot point.

The head set also includes a mouthpiece. The mouthpiece defines a bulb that is dimensioned to fit inside a user's mouth. The bulb is connected proximate the distal end of the articulating arm. The bulb is fabricated from an elastomeric material. Examples of elastomeric materials include polyisoprene rubber, chloroprene rubber, neoprene, styrene butadiene rubber, acrylonitrile butadiene rubber, ethylene propylene diene methylene, polyvinylchloride, polyethylene, polyurethane, urethane-coated nylon, ethyl vinyl acetate, and combinations thereof.

The mouthpiece has a plurality of cells embedded therein. The cells are configured to receive pressure applied by the tongue of an individual. In one embodiment, the mouthpiece comprises at least three outer cells, with the cells being disposed radially around a centerpoint. The centerpoint may simply be a geographical point of centricity, or it may define a separate cell. The cells are separated by walls fabricated within the mouthpiece.

Each of the cells contains a fluid. The fluid may be air or some other inert gas. In this instance, the cells may be referred to as air cells. Alternatively or in addition, the fluid may be water or other non-toxic liquid. In this case, the cells are fluid cells. For ease of reference, the cells will be described herein as simply that—cells.

The head set also includes a plurality of tubes. Each tube has a proximal end and a distal end. The distal end of each of the tubes is in substantially sealed fluid communication with a corresponding cell. This may be by means of an integral connection between the distal end of the tubes and respective walls. More preferably, a manifold (such as manifold 130 of FIG. 1) is provided that joins ends of tubes together to form the plurality of tubes.

Each of the plurality of tubes may generally reside at ambient pressure. Alternatively, and by way of example only, each of the plurality of tubes may be pre-loaded at a pressure of about 15 psi to 25 psi.

A plurality of transducers is also provided as part of the head set. Each transducer is in substantially sealed fluid communication with the proximal end of a corresponding tube. The transducers convert changes in pressure within the respective cells to corresponding electrical signals. Such electrical signals may be, for example, voltage signals, current signals, or resistive changes. The transducers are preferably in the nature of pressure sensors.

The head set may further include a processor. The processor serves to process the electrical signals. The electrical signals, such as voltage signals, are modulated to generate a pressure profile from the cells. The pressure profile represents a magnitude of pressure within the cells, a direction of pressure, a duration of pressure, or combinations thereof.

Preferably, the processor and the transducers reside separate from the head set. However, it is within the scope of the inventions herein to place the transducers and, optionally, the processor with operational software into the head set as an integrated unit.

The processor may be in operational electrical communication with a motor. For example, the processor may send instructions that cause the motor to move an object such as a bed, a door or a wheelchair. Alternatively, the processor may be in operationally electrical communication with a switch. The switch changes the electrical state of an appliance such as a light fixture, a television or a thermostat. Alternatively still, the processor may be in electrical communication with a cursor on a display. The display may have a digital keyboard that allows a user to "type" a message or "click" on a symbol.

The processor is preferably in communication with a display. In this embodiment, the display provides a visual platform for the movement of a cursor in accordance with the pressure profile. The cursor is manipulated by application of pressure on the cells by lingual movement over symbols. "Clicking" a symbol activates a motor on a device or changes the state of an electrical appliance.

In any instance, a magnitude of each electrical signal from the transducers may be recorded as part of the pressure profile over a specified period of time. The pressure profile is based upon pressure readings from the various cells. In one aspect, pressure signals are processed such that each electrical signal represents a pressure reading from a corresponding cell. Electrical signals associated with one or more corresponding cells are averaged over a specified period of time to produce the pressure profile. The pressure profile has a peak indicative of location at which pressure is being generated within the one or more cells during the specified period of time.

A method for moving a cursor using lingual manipulation is also provided herein. The method first includes providing a head set for a user. The head set is designed in accordance with the head set described above in any of its embodiments. In this respect, the head set has a head piece, and an articulating arm extending from the head piece. The articulating arm has a distal end.

The head set also includes a mouthpiece. The mouthpiece defines an elastomeric bulb that is connected proximate the distal end of the articulating arm. The bulb has a plurality of cells embedded therein for receiving pressure applied by the tongue of a user. The cells may be, for example, air cells.

The head set also includes a plurality of tubes. Each tube has a proximal end and a distal end. The distal end of each of the tubes is in substantially sealed fluid communication with a corresponding cell. The head set then also includes a plurality of transducers. Each transducer is in substantially sealed fluid communication with the proximal end of a corresponding tube. The transducers convert changes in pressure within the respective cells to corresponding electrical signals. Such electrical signals may be, for example, voltage signals, current signals, or resistive changes. The transducers are preferably in the nature of pressure sensors.

The head set further includes a processor. The processor serves to process the electrical signals. The electrical signals, such as voltage signals, are modulated to generate a pressure profile from the cells. The pressure profile represents a magnitude of pressure within the cells, a direction of pressure, a duration of pressure, or combinations thereof.

The pressure profile is based upon pressure readings from the various cells. In one aspect, pressure signals are processed such that each electrical signal represents a pressure reading from a corresponding cell. Electrical signals from one or more corresponding cells are averaged over a specified period of time to produce the pressure profile. The pressure profile has a peak indicative of location at which pressure is being generated within the one or more cells during the specified period of time.

The method also includes placing the plurality of tubes in fluid communication with the corresponding plurality of transducers. In addition, the method includes placing the processor in operative electrical communication with a cursor on a display. This allows a user to cause the cursor on the display to move in accordance with the pressure profile. Thus, the object that is initially moved is a cursor.

Preferably, the method also includes providing one or more symbols on the display. The user may "click" on a symbol using the cursor as controlled by the user's tongue. The symbol on the display comprises a picture, one or more alphanumeric characters, an arrow, a geometric figure, or combinations thereof.

In one embodiment, the processor is in electrical communication with a motor for moving an object. In this instance, one of the one or more symbols on the display corresponds to the object. The object may be, for example a bed, a wheelchair, or a door. The user may "click" on a symbol using the cursor and their tongue to, for example, cause the door to close or to cause the wheelchair to move.

Alternatively, the processor is in electrical communication with an appliance. In this instance, one of the one or more symbols on the display corresponds to the appliance. The appliance may be, for example, a light fixture, a television, or a thermostat. The user may "click" on a symbol using the cursor and their tongue to, for example, cause the light to dim or to turn on and off.

Preferably, the display presents a digital keyboard. This allows the user to move the cursor using lingual manipulation in order to select a series of characters on the keyboard. In this way, the user may compose a textual message. The method then includes the step of providing a "send" symbol on the display that, when selected by the user, sends the textual message through a wireless communications system.

In one aspect, a magnitude of each electrical signal is recorded as part of the pressure profile over the specified period of time. The cursor is then caused to be moved on a display in the direction indicated by the pressure profile at a velocity that corresponds to the magnitude of the electrical signals. In another aspect, an application of pressure by a patient on the centerpoint for a specified period of time and at a specified magnitude causes a location of the cursor to be reset to a beginning point on the display. Alternatively, an application of pressure by a patient on a selected outer cell for a specified period of time and at a specified magnitude causes a location of the cursor to be moved to a corresponding location on the display.

Finally, a method of typing characters on a virtual keyboard using lingual musculature is provided herein. In one embodiment, such method includes providing a head set as generally described above. The method further includes placing the plurality of tubes in fluid communication with the corresponding plurality of transducers. Preferably, each of the plurality of transducers is a pressure sensor having a diaphragm that is sensitive to changes in pressure within a tube. These changes are then delivered as electrical signals.

The method also includes placing the processor in operative electrical communication with a display. The display includes a digital keyboard. A cursor on the display is caused to move in accordance with the pressure profile. The cursor is used to select characters on the virtual keyboard. The selected characters on the virtual keyboard are "clicked" using the mouthpiece. In this way, the user may compose a textual message one character at a time.

BRIEF DESCRIPTION OF THE DRAWINGS

So that the manner in which the present invention can be better understood, certain illustrations, charts and/or flow charts are appended hereto. It is to be noted, however, that the drawings illustrate only selected embodiments of the inventions and are therefore not to be considered limiting of scope, for the inventions may admit to other equally effective embodiments and applications.

In FIG. 5A, the display shows a cursor that may be moved on a display. The cursor is moved through lingual manipulation in order to operate a wheelchair or other mechanical device.

In FIG. 5B, the display also shows a cursor that may be moved on a display. Here, the cursor is moved through lingual manipulation in order to change the status of an electrical appliance.

In FIG. 5C, the display again shows a cursor that may be moved on a display. Here, the cursor is moved through lingual manipulation in order to "press" or "click" on keys from a virtual keyboard.

FIGS. 6A and 6B provide a single flowchart for a method for moving a cursor on a display using lingual manipulation, in one embodiment. The flowchart offers alternate final steps for causing an external action.

DETAILED DESCRIPTION OF CERTAIN EMBODIMENTS

Definitions

As used herein, the term "cursor" means any indicator of a position on a computer screen or display. The cursor may be, for example, a flashing bar, an underline, or an arrow or other symbol.

DESCRIPTION OF SPECIFIC EMBODIMENTS

Figure 1:
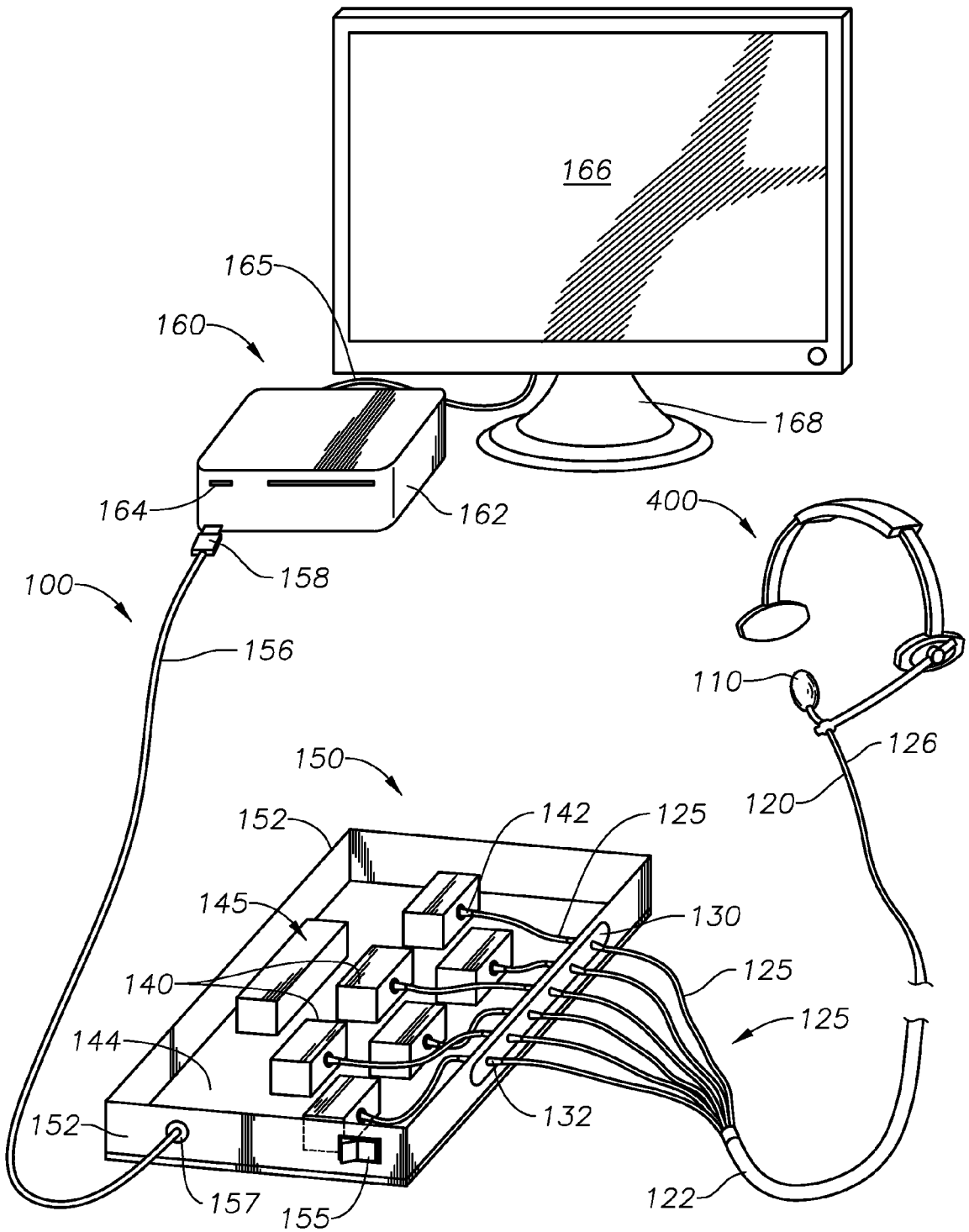
FIG. 1 is a perspective view of an intra-oral system according to the present invention, in one embodiment. A head set is seen as part of the system, with the head set having a bulbous mouthpiece.

FIG. 1 is a perspective view of an intra-oral system 100 according to the present invention, in one embodiment. Various components of the system 100 are shown. The components first include a head set 400, shown in one embodiment. The head set 400 is designed and configured to be worn on the head (not shown) of a user. The user is preferably an individual who has lost function of at least their hands and, possibly, additional portions of their upper extremities. However, the head set 400 may be worn by any individual.

The system 100 includes various other components such as a mouthpiece 110, a plurality of tubes 125, a manifold 130, a plurality of corresponding transducers 140, a processor 145, an operational box 150 or housing, a computer 160, and a display 166. Some of these components may be described and claimed herein as being part of the head set 400 as they are operationally related.

Figure 4:
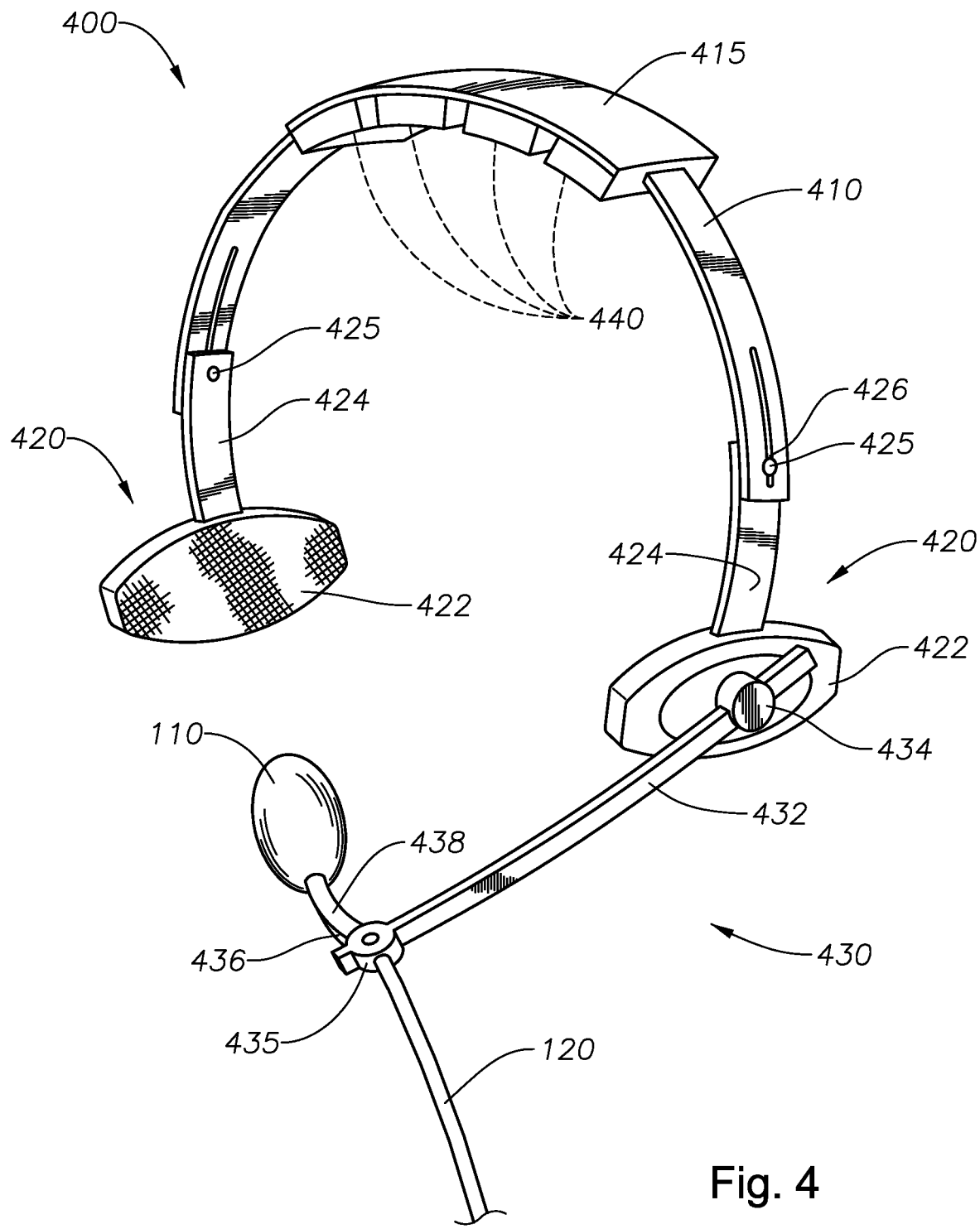
FIG. 4 is a perspective view of the head set of the present invention, in one embodiment.

FIG. 4 provides a perspective view of the head set 400. Here, the head set 400 is shown apart from the intra-oral system 100. The head set 400 first includes a support member 410. The support member 410 defines an arcuate or arched member configured to rest on the crown of an individual user's head. The support member 410 optionally includes a central cushioning member 415.

The head set 400 also includes opposing head rests 420. In the arrangement of FIG. 4, the head rests 400 each include pads 422 and supporting bars 424. The supporting bars 424 include pins 425. The pins 425 slidably move through slots 426 in the support member 410. In this way, one or both of the head rests 420 is adjustable relative to the head set 400.

The head set 400 also includes an articulating arm 430. In the arrangement of FIG. 4, the articulating arm 430 has a first arm portion 432 and a second arm portion 438. The first arm portion 432 has a proximal end 434 slidably and pivotally connected to one of the pads 422. The first arm portion 432 also has a pivot point 435 opposite the proximal end 434.

The second arm portion 438 pivots from the pivot point 435 of the first arm portion 432. Opposite the pivot point 435, the second arm portion 436 has a distal end 438. The mouthpiece 110 is connected to the articulating arm 430 at the distal end 438.

It is understood that the configuration of the head set 400 and its articulating arm 430 are merely illustrative. Other designs and arrangements may be employed. What is important is that the head set 400 be designed to allow the mouthpiece 110 to reach the mouth of the user.

The mouthpiece 110 is configured to be selectively inserted into an individual's mouth (not shown). As noted, the individual is preferably a person who has limited use of their upper extremities. However, the individual may also be may be a patient who is in need of therapy to develop the intra-oral musculature. Such a patient may be, for example, a stroke victim or the victim of a head or neck injury. Alternatively, such a patient may be a child who suffers from congenital limitations in chewing and/or swallowing food.

The mouthpiece is preferably fabricated from an elastomeric material. Suitable materials may include polyisoprene rubber, chloroprene rubber, neoprene rubber, styrene butadiene rubber, and acrylonitrile butadiene rubber. Additional suitable examples include silicone, ethylene propylene diene methylene, polyvinylchloride, polyethylene, polyurethane, urethane-coated nylon, and ethyl vinyl acetate. Combinations of these materials may also be employed.

Figure 2A:
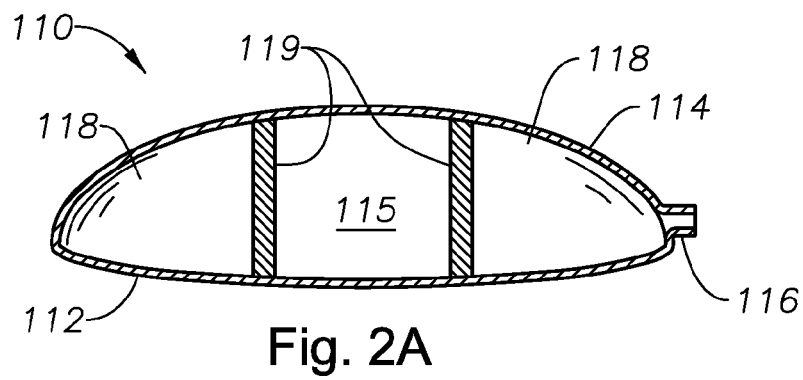
FIG. 2A is a cross-sectional view of the mouthpiece from the intra-oral system of FIG. 1, in one embodiment. The cross-section is taken across a major axis of the mouthpiece.
Figure 2B:
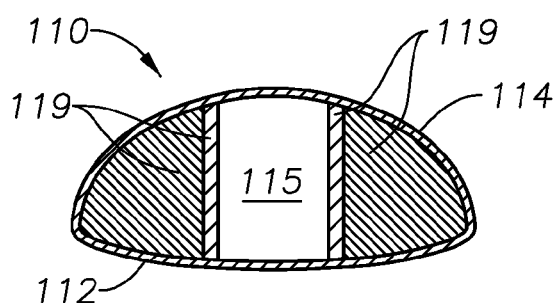
FIG. 2B is another cross-sectional view of the mouthpiece from the system of FIG. 1. Here, the cross-section is taken across a minor axis of the mouthpiece.
Figure 2C:
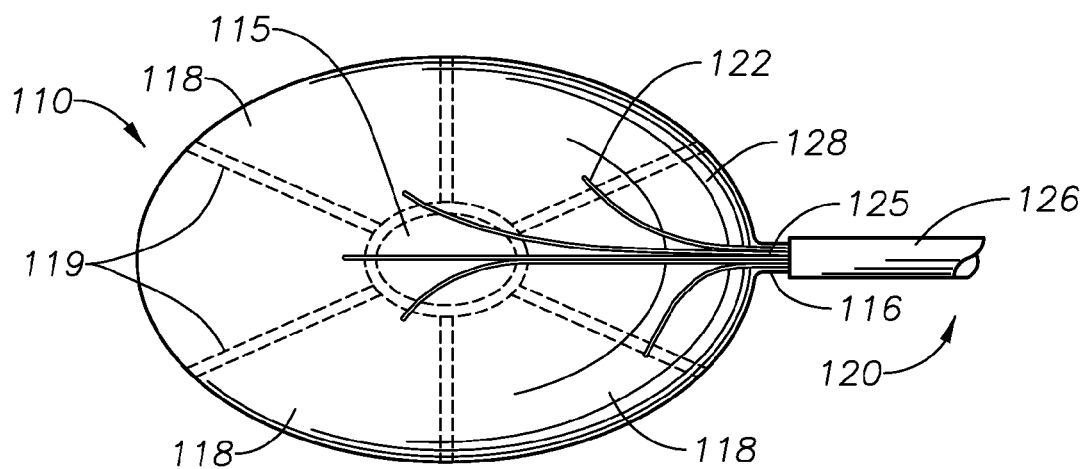
FIG. 2C is a top view of the mouthpiece from the system of FIG. 1. Individual air cells are shown along with corresponding air tubes.

Enlarged views of the mouthpiece 110 are provided in FIGS. 2A through 2C. FIG. 2A is a cross-sectional view of the mouthpiece 110 from the system of FIG. 1 and the head set 400 of FIG. 4, in one embodiment. The cross-section is taken across a major axis. FIG. 2B is another cross-sectional view of the mouthpiece 110. Here, the cross-section is taken across a minor axis. FIG. 2C is a top view of the mouthpiece 110 from the system of FIG. 1 and the head set 400 of FIG. 4. Features of the mouthpiece 110 will be discussed with reference to these three figures together.

The mouthpiece 110 is designed to be substantially hollow. To this end, the mouthpiece 110 defines a bottom surface 112 and a top surface 115. The bottom surface 112 is preferably substantially flat while the top surface 115 is preferably curved to create an arcuate profile. Thus, the mouthpiece 110 is in the nature of a bulb.

The mouthpiece 110 also includes a plurality of cells 115, 118. In the arrangement of FIGS. 2A through 2C, six cells 115, 118 are provided. These represent a central cell 115 and then separate cells 118 spaced radially around the central cell 115. Preferably, at least three radial cells 118 are provided. In the illustrative arrangement of FIGS. 2A through 2C, the mouthpiece 110 has five radial cells 118. The radial cells 118 preferably are equi-radial in dimension, meaning that each cell 118 forms a substantially equal angle extending from a center point of the mouthpiece 110.

Each of the cells 115, 118 is filled with a fluid. The fluid may be a compressible fluid, or gas. The compressible fluid may be air or another inert gas. The compressible fluid may comprise oxygen, carbon dioxide, nitrogen, or combinations thereof. Alternatively, the fluid may be a substantially non-compressible fluid, such as water or other non-toxic liquid. A combination of compressible and non-compressible fluids may also be employed. In any instance, fabrication of the intra-oral system 100 will typically involve establishing a baseline pressure between the cells 115, 118 and electronics, as discussed more fully below. This establishes a more accurate conversion of pressure changes to electrical signals by the transducers 140.

Each cell 115, 118 holds a volume of fluid. Preferably, the fluid is held at ambient pressure. Alternatively, the fluid in the cells 115, 118 is pre-loaded at a higher pressure such as between about 15 psi and 25 psi. In this way, the mouthpiece 110 is at least nominally resistive to pressure placed by the patient using his or her tongue.

To define the cells 115, 118, the mouthpiece 110 includes a series of walls 119. The walls 119 are sealed between the bottom surface 112 and the top surface 115. Sealing may be through heat sealing, RF sealing, or other mechanisms known in the art of plastic injection molding or other molding techniques.

The mouthpiece 110 may be configured in different sizes. The size will primarily be dictated by the size of the individual user's mouth. It is noted that for smaller users, fewer cells may be necessitated due to size limitations. The number of cells will affect the manner in which the intra-oral system 100 is programmed.

Referring back to FIG. 1, the head set 400 also includes a plurality of tubes 125. A tube 125 is provided to correspond to each radial cell 118. Optionally, a tube 125 is also provided for the central cell 115. The tubes 125 are sealingly disposed within the walls 119 of the mouthpiece 110. The tubes 125 are preferably manufactured to be integral to respective walls 119.

It is noted that in the mouthpiece 110 of FIG. 2C, the central cell 115 receives a tube 125. However, in some embodiments the central cell 115 may be dead, meaning that it does not receive its own tube 125. Indeed, in another arrangement, the central cell 115 holds no fluid, but just defines a center point in the mouthpiece 110.

The tubes 125 exit the mouthpiece 110 through an end opening 116. The end opening 116 defines a circular orifice that frictionally and, optionally, sealingly receives a bundle of tubes 125. The tubes 125 extend from respective walls 119, travel through an end area 128 of the mouthpiece 110 (which is not a cell), travel through the end opening 116, and then exit the mouthpiece 110.

In the mouthpiece 110 of FIG. 2C, the tubes 125 connect to the walls 119 internal to the mouthpiece 110, that is, through the end area 128 and through the central cell 115. However, some or all of the tubes 125 may alternatively enter the cells 115, 118 from a top, a bottom or an outer edge of the bulb defining the mouthpiece 110. The present inventions are not limited by the method of providing fluid communication between the tubes 125 and the cells 115, 118 unless so provided in the claims.

In the arrangement of FIG. 1, the tubes 125 are optionally bundled as they exit the mouthpiece 110. That means that the tubes 125 are held together externally by a tubular sheath 120. The tubular sheath 120 is also seen in FIG. 4 extending from the pivot point 435. Of course, the tubular sheath 120 need not travel through the pivot point 435 of the head set 400.

Figure 3:
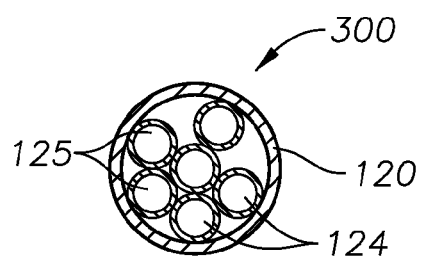
FIG. 3 is a cross-sectional view of the air tube bundle from the system of FIG. 1, in one embodiment.

FIG. 3 is a cross-sectional view of a tube bundle 300 from the system of FIG. 1, in one embodiment. In the arrangement of FIG. 3, the tube bundle 300 includes a tubular sheath 120. The tubular sheath 120 helps to protect the tubes 125 and keeps them from getting punctured or tangled. Six illustrative tubes 125 are seen within the tubular sheath 120. Each tube 125 defines a channel through which fluid passes. It is understood that any number of tubes 125 and corresponding cells 115, 118 may be used in the system 100.

Referring again to FIG. 1, the system 100 also includes a plurality of transducers 140. The transducers 140 are in the nature of pressure sensors. The transducers 140 may be, for example, ASDX pressure sensors made by the Sensing and Control Division of Honeywell in Golden Valley, Minn. The ASDX series of pressure sensors utilize a small internal diaphragm for sensing fine variations in pressure. Different sensors are offered in the series for sensing within different pressure ranges. Such ranges include 0 to 1 psi, 0 to 5 psi, 0 to 15 psi, and 0 to 30 psi. The ASDX sensors offer a high level output (5.0 Vdc span) that is fully calibrated and temperature compensated with on-board Application Specific Integrated Circuitry (ASIC).

The transducers 140 are preferably housed within an operational box 150. The box 150 has walls 152 and a top (not shown). The operational box 150 will include an electrical circuit board 144 that places the transducers 140 in electrical communication with one another as well as with a power supply. A power switch for the operational box 150 is seen at 155.

The transducers 140 are in fluid communication with respective cells 115, 118. This is done by means of the tubes 125. A proximal end of each tube 125 is connected to a transducer 140 at a connection point 142, while a distal end of each tube 125 is connected to a respective cell 115, 118, preferably at or through a respective wall 119 in the mouthpiece 110.

Each of the tubes 125 may extend unbroken from a transducer 140 to a cell 115 or 118. However, it is preferred that a manifold 130 be provided to enable connections of tubes 125 inside and outside of the operational box 152. The manifold 130 may include a plurality of prongs 132. In one aspect, each of the prongs 132 extends from the wall 152 of the operational box 150 and defines a channel that extends from each side of the manifold 130. This means that each prong 132 is actually a pair of prongs, with one prong of a pair of prongs extending inside of the operational box 152, and another prong of the pair of prongs extending outside of the operational box 152. In this way, each pair of prongs 132 enables fluid communication through the tubes 125 without necessity of the operator opening the box and exposing the delicate transducers 140. Further, the therapist or other operator is not required to manipulate the fragile connection 142 between the tubes 125 and the respective transducers 140. Preferably, the tubes 125 are color-coded with the prongs 132 so that the tubes 125 properly correspond to the correct transducers 140. Alternatively, other coding systems may be used such as alphabetical or numeric associations, or the use of symbols. Alternatively still, custom connectors which connect the tubes 125 to the prongs 132 in only one orientation may be utilized.

It is noted again that the tubes 125 are preferably bundled by a tubular sheath 120. The tubular sheath 120 extends generally from the manifold 130 to the end opening 116 of the mouthpiece 110. A proximal end 122 of the tubular sheath 120 begins near the manifold 130, while a distal end 126 of the tubular sheath 120 covers the end opening 116 of the mouthpiece 110. In this way, the mouthpiece 110, the tubes 125 outside of the operational box 152, and the tubular sheath 120 are essentially one integral unit. Each patient is supplied with his or her own mouthpiece 110 having integrated tubes 125 and the tubular sheath 120. The only "assembly" required by the therapist is to connect the tubes 125 with the external prongs 132 on the manifold 130.

In the arrangement of FIG. 1, the transducers 140 are shown external to the head set 400, meaning they are not mechanically supported by the head set 400. However, in an alternate arrangement the transducers are integrated into the head set 400. In the arrangement of FIG. 4, transducers 440 may be placed inside of the cushioning member 415. Dashed lines are shown to indicate the optional placement of transducers 440. This arrangement is not preferred as it would require connecting air tubes 125 over or behind the user's head and into the head set 400 itself.

In any arrangement, the transducers 140 are designed to convert changes in pressure within the cells 115, 118 to electrical signals. The electrical signals may be analog voltage signals. Other examples of electrical signals that may be used include current signals or resistive changes. The changes in pressure within the cells 115, 118 are delivered pneumatically or fluidically, depending on the fluid used, to the transducers 140 through the respective tubes 125. As the transducers 140 sense an increase in pressure, a corresponding voltage or other electrical signal is delivered through the electrical circuit board 144.

The intra-oral system 100 (and, operationally, the head set 400), also includes a processor 145. The processor 145 uses operational software for processing the electrical signals. As shown in the arrangement for the system 100 of FIG. 1, the electrical signals are delivered to the processor 145 by means of the electrical circuit board 144. This means that the processor 145 also resides within the operational box 150. However, in another embodiment the processor 145 resides outside of the operational box 150. In yet another arrangement, electrical signals may be sent through a wireless connection such as through the use of Bluetooth technology. In yet another arrangement, the processor 145 may reside on the head set 400 itself.

In any instance, the electrical signals, such as voltage signals, are modulated to generate a pressure profile from the cells 115 and/or 118. The pressure profile represents a magnitude of pressure from within the cells 115 and/or 118. Alternatively or in addition, the pressure profile represents a location or direction of pressure within the cells 115 and/or 118. Alternatively or in addition, the pressure profile represents a duration of pressure applied to the cells 115 and/or 118.

The pressure profile is based upon pressure readings from the various cells, either individually or through some combination. In one aspect, pressure signals are processed such that each electrical signal represents an air pressure reading from a corresponding cell. Electrical signals from one or more corresponding cells may be averaged over a specified period of time to produce the pressure profile. The pressure profile has a peak indicative of location at which pressure is being generated within the one or more cells during the specified period of time.

The pressure profile can be used to determine direction. A curve-fitting technique may be used to determine the peak pressure, yielding a representation of the radial direction from 0 to 360 degrees. A windowed statistical analysis approach may also be employed for highly accurate measurements.

The pressure profile can be used to determine the magnitude of pressure applied by the patient. The preferred method is to use the average value of the pressure profile across all cells 115, 118 to represent this magnitude. In certain scenarios, the associated pressure value from the central air (or fluid) cell 115 can be solely used to determine the magnitude. A baseline or steady-state value representing no pressure being applied to the mouthpiece 110 may be subtracted from the pressure profile to more accurately determine the actual pressure applied by the patient.

When a pressure profile is generated, a normalization procedure may be used to remove differences in pressure-to-voltage characteristics between cells. These differences can arise due to manufacturing imperfections in the cells 115, 118 and/or the electronics. Differences can also arise due to incidental variations in fluid volume within the cells 115, 118 and associated tubes 125. The normalization values can be stored on the processor 145 and/or a computer, seen at 160.

An electrical cord 156 extends from the operational box 150. The cord 156 extends from an opening 157 in the operational box 152. The cord 156 preferably has a USB connector 158 for placing the processor 150 in electrical communication with a computer 160. More specifically, the USB connector 158 places the processor 145 in electrical communication with a processing unit 162 for a computer 160.

The computer 160 is preferably a general purpose computer 160. Such a computer may be a laptop computer or a desk top computer as may be purchased at a local retail store. In this instance, communications software may be loaded onto the processing unit 162 by the therapist or IT representative or field representative. However, the processing unit 162 may be a specially designed or dedicated unit that comes with the operational box 150. Alternatively, the processing unit 162 may be a central processing unit that is part of a network.

In operation, the system 100 preferably allows a patient to manipulate a cursor on a screen. This is done by the patient moving his or her tongue across and against the bottom surface 112 of the mouthpiece 110. Such movement causes an increase in pressure within selected cells 115, 118. The increase in pressure causes a corresponding increase in pressure within the tubes 125. The pressure changes, in turn, are transmitted to the respective transducers 140 within the operational box 150.

Electrical signals are generated by the transducers 140 in response to the changes in pressure within the tubes 125. These signals are sent to the processor 145. The processor 145, in turn, modulates the signals and sends them to display software residing on the processing unit 162. Using the display, a cursor (or other object not shown in FIG. 1) is caused to be moved across a display 166. Manipulation of the cursor allows the user to move or to actuate a separate object external to the system 100, or to cause an external action.

To implement this function, the system 100 also includes the visual display 166. The display 166 represents a screen for visualizing the cursor as it is moved by the user. The display 166 may include a stand 168 for supporting the display 166. Preferably, the display 166 is adjustable to accommodate the height or position of the user. A cord 165 is offered to provide the needed electrical communication between the processing unit 162 and the display 166 when the two are not part of an integral device such as a laptop computer.

It is understood that the display 166 arrangement of FIG. 1 is merely illustrative. The display 166 may be part of a laptop computer. Alternatively, the display 166 may be part of a headset, or may comprise a large, wall-mounted screen. Alternatively still, the display 166 may be a screen that receives an image from a projector.

Figure 5A:
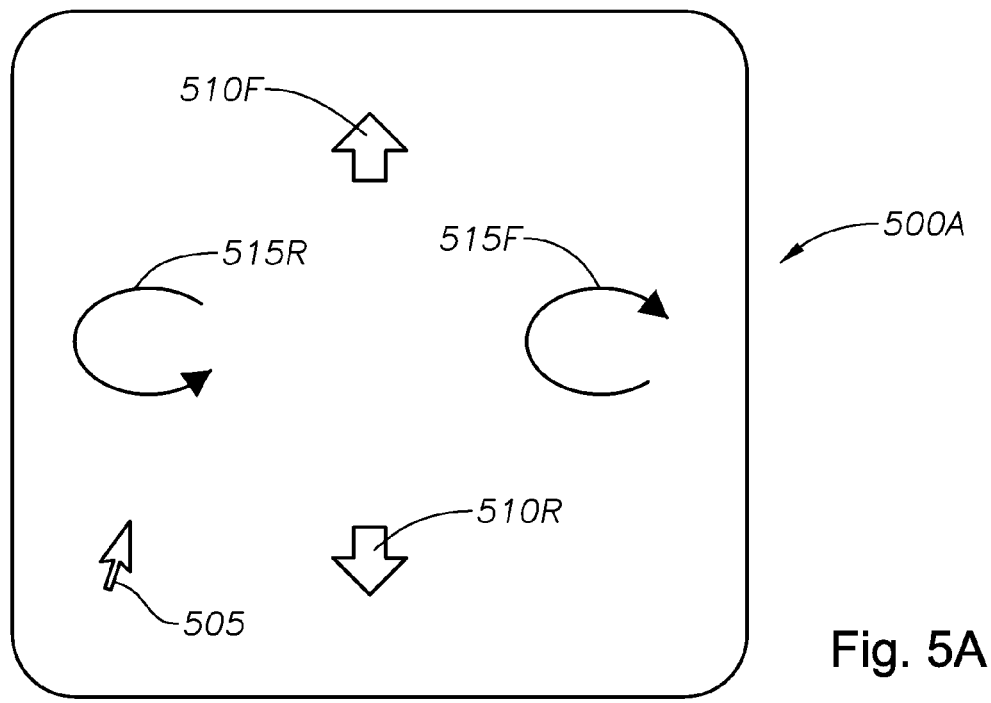
FIGS. 5A through 5C present various arrangements for displays from the system of FIG. 1.
Figure 5B:
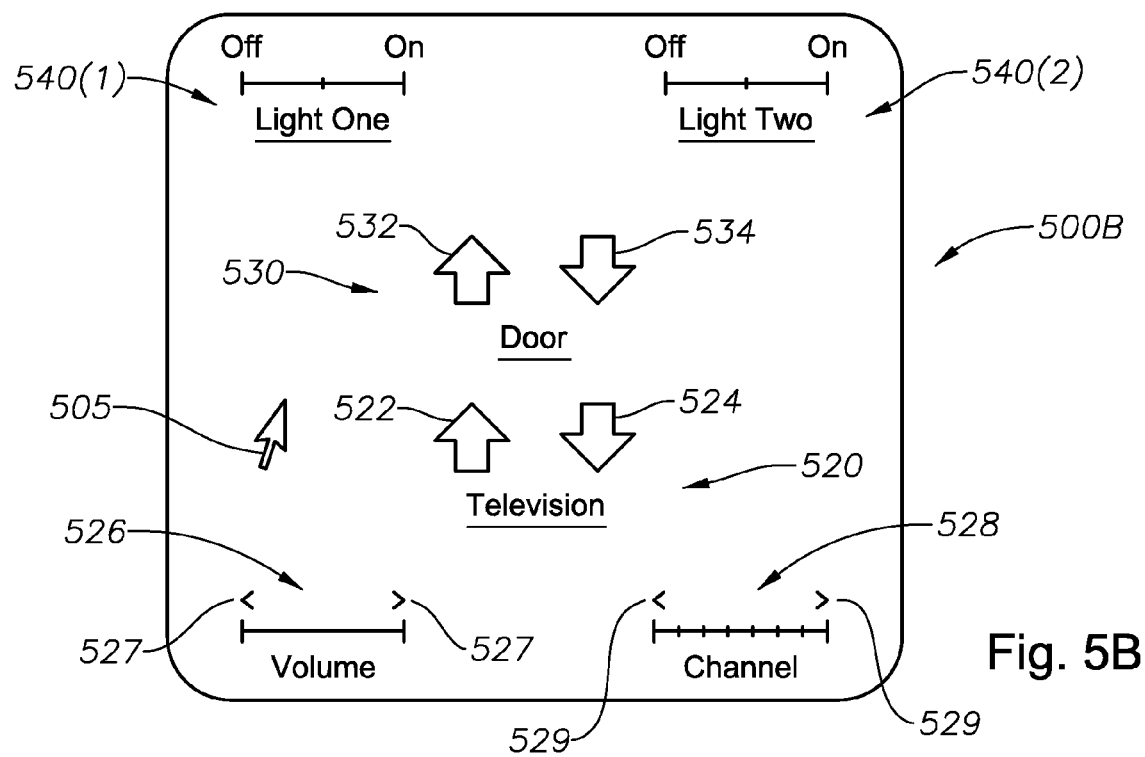
Figure 5C:
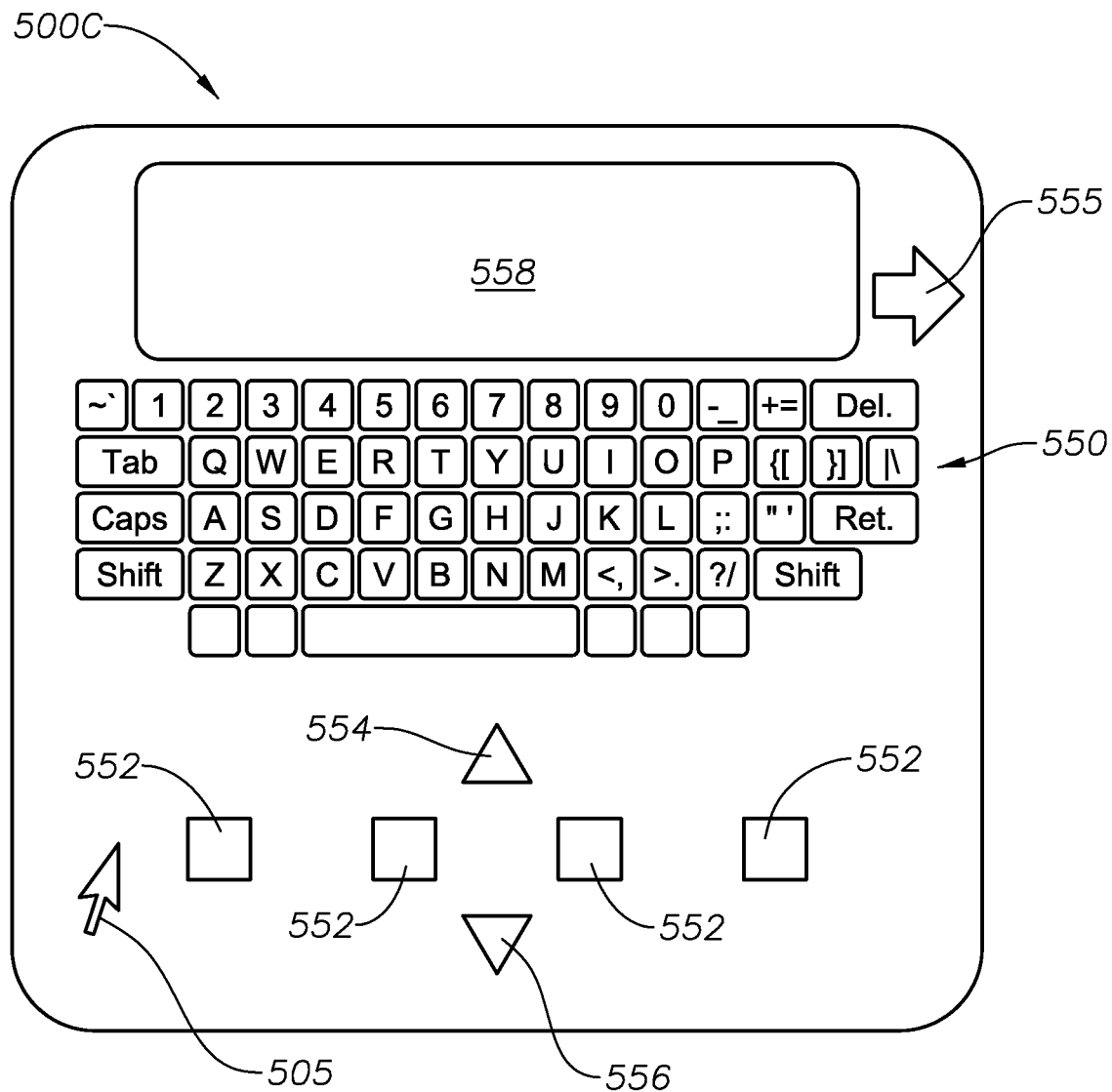

FIGS. 5A through 5C present various arrangements for displays from the system of FIG. 1. FIGS. 5A through 5C also demonstrate methods for using the head set 400 and attached mouthpiece 110.

First, FIG. 5A demonstrates how the head set 400 and attached mouthpiece 110 may be used for moving a mechanical object, in one embodiment. FIG. 5A specifically shows a display 500A. In this system, a cursor is shown at 505. The cursor 505 is used to move an object by the user through lingual manipulation in accordance with the pressure profile. As the user applies pressure to the various air cells in the bulb defining the mouthpiece 110, the cursor 505 is moved across the display 500A. Thus, the mouthpiece 110 becomes a "mouth mouse."

The display 500A is arranged for the purpose of allowing the user to move an external object. In this instance, the individual may use the system 100 to operate a wheelchair. Alternatively, the individual may use the system 100 to manipulate the position of a bed or to open or close a door.

The display 500A includes directional keys. In this arrangement, the directional keys are used to move a wheelchair (not shown). The illustrative directional keys represent forward 510F and reverse 510R arrows. Actuation of these arrows 510F, 510R causes the wheelchair (or other object) to move forward or backward. The directional keys also represent clockwise 515F and counter-clockwise 515R arrows. Actuation of these arrows 515F, 515R causes the wheelchair to rotate clockwise or counter-clockwise.

The keys 510F, 510R, 515F, 515R are activated by using the cursor 505. In one aspect, a symbol 510F, 510R, 515F, or 515R is activated by the user positioning the cursor 505 over the selected symbol 510F, 510R, 515F, 515R, and then double-clicking on the center cell 115. In another aspect, a symbol 510F, 510R, 515F, or 515R is activated by the user positioning the cursor 505 over the selected symbol 510F, 510R, 515F, 515R, and then pressing against the center cell 115 for a designated period of time at a certain level of pressure. In the instance where the center cell 115 is "dead" or where there is no center cell, a symbol 510F, 510R, 515F, or 515R may be activated by the user positioning the cursor 505 over the selected symbol 510F, 510R, 515F, 515R, and then pressing the center of the mouthpiece 110 for a designated period of time at a certain level of pressure.

The display 500A of FIG. 5A is ideally supported on the individual's wheelchair. For example, the display 500A will be mounted on an arm rest (not shown). At the same time, the mouthpiece 110 is part of the head set 400 so that the mouthpiece 110 is at all times in proximity to the user's mouth. In this way, the individual may selectively insert the mouthpiece 110 into their mouth for movement of the wheelchair (or other object). In addition, the operational box 150 for the transducers 140 and the processor 145, along with the screen 166, are positioned together on the wheelchair or on the bed or even on the head set 400, depending on the arrangement.

It is understood in this application that the display 166 will be in electrical communication with a motor or servo-system on the wheelchair. In this way, the user's instructions delivered by moving the cursor 505 on the screen 500A cause the wheelchair to respond. Of course, the display 500A may be used to control mechanical objects other than a wheelchair. For example, symbols 510F, 510R, 515F, 515R may be used to move a bed, open and close a door, and the like.

As an alternative, the user may use the head set 400 and connected mouthpiece 110 to manipulate a mechanical object without need of a display 400A. For example, simple pressing of the mouthpiece 110 at a designated pressure and/or for a designated period of time may automatically cause the wheelchair to move, or cause a door to be opened, turn on a light, or control another object. Thus, "moving" of an object herein encompasses moving the object with or without a symbol on a display. The object may be a cursor itself, or may be an external object.

The system 100 may be used by a physically-limited individual to operate other apparatus' besides a mechanical object. Such apparatus' may include electrical appliances, such as a television, a light fixture, or a thermostat.

FIG. 5B presents a display 500B for the system 100, in an alternate embodiment. A cursor is again shown at 505. The cursor 505 is used to change the status of an electrical appliance by the user through lingual manipulation in accordance with the pressure profile. The display 500E shows arrow 522 for turning on a television, and arrow 524 for turning off a television. The display 500B also shows carrots 527 for adjusting the volume of the television, and carrots 529 for changing the channel.

The display 500B also shows bar 540(1) for turning a first light fixture on and off, and bar 540(2) for turning a second light fixture on and off. The bar configuration 540(1) and 540(2) may also serve a rheostat, thereby adjusting the brightness of a light fixture. The display 500B also shows arrow 532 for opening a door, and arrow 534 for closing the door. This would be done through a servo-motor.

It is understood that displays 500A and 500B are merely illustrative. Other objects and appliances may be controlled through the use of a cursor and symbols. The user may then press or double-click on the center air cell 115 of the mouthpiece 110 to turn an object on or off or to adjust its status. A signal is then sent from the system 100 to the electrical apparatus. This signal is preferably a wireless signal such as through infrared technology, Bluetooth technology or other wireless technology that may be known to those of ordinary skill in the art.

FIG. 5C presents a display 500C for the intra-oral system 100, in yet an alternate embodiment. In this display 500C, a cursor is again shown at 505. The illustrative cursor 505 is an arrow. The cursor 505 is moved across the display 500C in accordance with the pressure profile. In this embodiment, the display 500C includes a keyboard 550. The keyboard 550 and other symbols in the display 500C are used to allow the individual to type text messages using just his or her mouth.

The display 500C includes symbols 552. These symbols 552 may be used, for example, to open and close a door (not shown) or to select an appliance to be controlled. Arrow keys 554, 556 are also provided on the display 500C. The user may manipulate a selected electrical apparatus or appliance by double-clicking on an arrow key 554, 556. For example, a light fixture may be brightened or dimmed by double-clicking on the arrow keys 554, 554. Alternatively, the channel of a television or radio may be changed by double-clicking on the arrow keys 554, 556. Separate arrow keys (not shown) may be used to then adjust the volume.

In lieu of double-clicking, a symbol 552 or an arrow key 554, 556, a function may be selected or activated by the user positioning the cursor 505 over the selected symbol 552 or arrow 554, 556, and then pressing against the center cell 115 for a designated period of time at a certain level of pressure. In the instance where the center cell 115 is "dead," a selected symbol 552 or key 554, 556 may be activated by the user positioning the cursor 505 over the selected symbol 552 or arrow key 554, 556, and then pressing against a designated radial cell 118 or in the centerpoint of the mouthpiece 110 for a designated period of time at a certain level of pressure.

A signal is sent from the system 100 to the electrical apparatus. This signal is preferably a wireless signal such as through infrared technology, Bluetooth technology or other wireless technology that may be known to those of ordinary skill in the art.

The keyboard 550 allows the physically-limited individual to type in a text message such as an e-mail message to another individual. The individual uses the cursor 505 to select alphanumeric keys to be "pressed." Pressing means double-clicking or otherwise applying pressure to a selected air or fluid cell in the mouthpiece 110. By selecting and "pressing" a series of digital keys on the keyboard 550, a message may be composed. The message may be seen on a visualization screen 558 on the display 500C. The message may then be "sent" by pressing a return arrow 555. In this arrangement, the processor has a wired or wireless internet connection for delivering the message through a communications network.

Figure 6A:
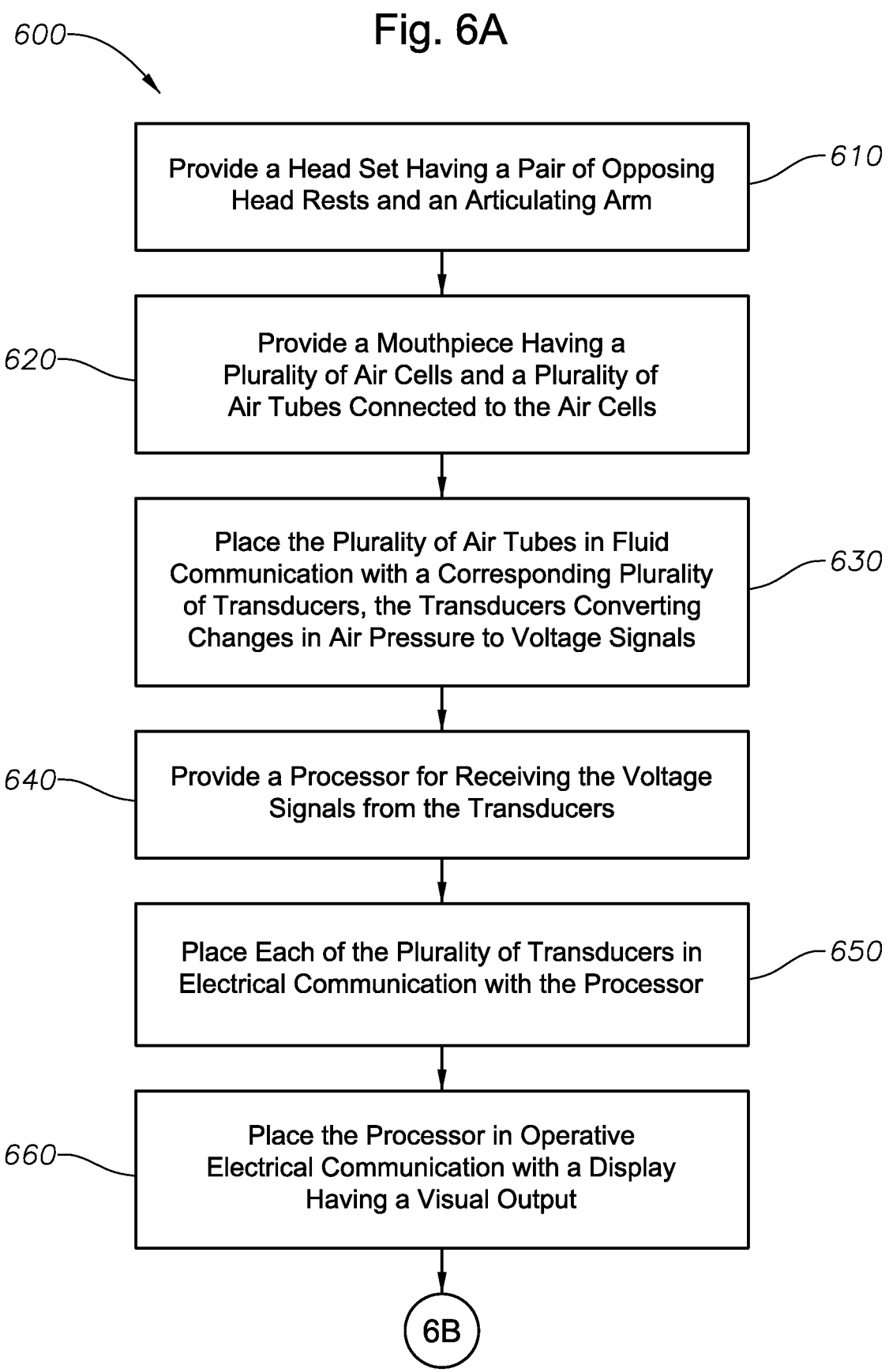

A method 600 for moving a cursor on a display using lingual manipulation is also provided herein. FIGS. 6A and 6B present a unified flow chart, showing steps for generally performing the method 600, in one embodiment.

The method 600 first includes providing a head set. This is shown at Box 610 of FIG. 6A. The head set is generally in accordance with the head set 400 described above, in its various embodiments. Generally, the head set will have a head piece, opposing head rests, and an articulating arm extending from the head piece and having a distal end.

The method 600 further includes providing a mouthpiece. This is provided at Box 620. The mouthpiece is part of the head set, and serves as a "mouth mouse." The mouthpiece defines an elastomeric bulb, and is connected proximate the distal end of the articulating arm.

In one aspect, the mouthpiece comprises at least three outer cells disposed radially around a centerpoint. The centerpoint may define a separate cell, or it may be a "dead" area. The cells are divided and sealed by walls.

The mouthpiece has a plurality of fluid-containing cells. The fluid may be a compressible fluid, or gas. The compressible fluid may be air or another inert gas. Alternatively, the fluid may be a substantially non-compressible fluid, such as water or other non-toxic liquid. A combination of compressible and non-compressible fluids may also be employed. In any aspect, the fluid-containing cells are embedded into the mouthpiece for receiving pressure applied by the tongue of an individual.

The head set will also include a plurality of tubes. Each tube has a proximal end and a distal end, with the distal end of each of the tubes being in substantially sealed fluid communication with a corresponding cell of the mouthpiece. In one aspect, each of the tubes comprises more than one tubular body operatively connected to form a single, pneumatically or fluidically sealed channel. In this instance, a manifold may be used to provide a "quick-connect" between sets of tubes.

Preferably, each of the plurality of tubes is an air tube that resides substantially at ambient pressure. Alternatively, each of the plurality of tubes may be preloaded at a pressure of about 15 psi to 25 psi. This creates desirable additional resistance for stronger users. It also provides flexibility for the operator in "tuning" the system so that pressure readings are accurate. The tubes preferably have an inner diameter of about 0.05 inches to 0.5 inches. However, other dimensions may be employed.

The method 600 also comprises placing each of the plurality of tubes in fluid communication with a corresponding transducer. This is provided at Box 630. Each transducer is preferably a pressure sensor having a diaphragm that is sensitive to changes in pressure within a tube. Each transducer is in sealed fluid communication with the proximal end of a corresponding tube. The transducers convert changes in pressure within the cells to voltage or other electrical signals. The changes in pressure within the cells are delivered pneumatically or fluidically to the transducers through the respective tubes.

The method 600 also includes the step of providing a processor. The processor receives the voltage signals from the transducers and processes them. This is shown in Box 640.

The method 600 further includes the step of placing each of the plurality of transducers in electrical communication with the processor. This is shown in Box 650. The processor may be placed within the same hardware packaging or box as the transducers. Alternatively, the processor may be a part of a laptop computer or a desktop computer.

The method 600 also includes the step of placing the processor in operative electrical communication with a display. This step is presented in Box 660. The display has a visual output that presents a cursor.

The method 600 also includes the step of generating a pressure profile from the cells. This step is provided in Box 670. The pressure profile is generated by the processor in response to the voltage or other electrical signals received from the transducers. The signals are modulated by the processor to generate a pressure profile from the cells. Preferably, the pressure profile represents a magnitude of pressure within the cells, a direction of pressure, a duration of pressure, or combinations thereof.

The pressure profile is based upon pressure readings from the various cells. In one aspect, pressure signals are processed such that each voltage signal represents an air pressure reading from a corresponding air cell. Voltage signals from one or more corresponding air cells are averaged over a specified period of time to produce the pressure profile. The pressure profile has a peak indicative of location at which pressure is being generated within the one or more cells during the specified period of time.

The processor sends signals based on pressure profiles to a processing unit. The processor may be part of a computer system. Signals are sent to the processing unit by means of a USB port or other electronic communications connection. Visualization software is pre-loaded onto the processing unit to enable the user to see an object being moved on a display.

The method 600 further includes the step of causing the cursor on the display to move. This is provided at Box 680 of FIG. 6B. The cursor is moved by means of lingual manipulation of the mouthpiece. More specifically, the user applies pressure to the various cells in the mouthpiece to ultimately cause translation of the cursor on the display.

The cursor is moved over a symbol that represents a mechanical device to be activated or an electrical appliance to be changed. The symbol on the display may be of any type. For example, the symbol may be a picture of an apparatus or appliance. Alternatively, the symbol may be one or more alphanumeric characters, an arrow indicating direction, or a geometric figure.

In order to move a cursor, a magnitude of each voltage signal is recorded as part of the pressure profile over the specified period of time. The object is then caused to be moved on the display in the direction indicated by the pressure profile at a velocity that corresponds to the magnitude of the voltage signals. In another aspect, an application of pressure by a user on the centerpoint for a specified period of time and at a specified magnitude causes a location of the object to be reset to a beginning point on the display. Alternatively, an application of pressure by a user on a designated outer cell for a specified period of time and at a specified magnitude causes a location of the object to be moved to a corresponding location on the display.

In one aspect, the signal processor receives voltage signals from each of the plurality of transducers. The processor processes the signals such that each voltage signal represents a pressure reading from a corresponding cell. Electrical signals from one or more corresponding cells may be averaged over a specified period of time to produce the pressure profile. The pressure profile may have a peak indicative of location at which fluid pressure is being generated within the one or more cells during the specified period of time.

Optionally, the method 600 includes selecting a symbol to actuate a mechanical device or an electrical appliance. This is shown at Box 690A. Alternatively, a series of symbols is selected in order to compose a textual message. This is shown at Box 690B.

To select a symbol, the cells within the mouthpiece may be configured to respond to double-clicking by the user. This means that the user moves his or her tongue against a particular cell or area of the mouthpiece twice within a designated period of time recognized by the processor. For example, double-clicking of application of pressure by a user on a centerpoint for a specified period of time and at a specified magnitude may cause actuation of a mechanical device or an electrical appliance, as discussed above. Alternatively, the user may simply hold pressure against the centerpoint for a specified longer period of time and at a specified magnitude over a symbol on the display.

As an additional step to Box 690B, the user may send the textual message through a wireless communications network. This is shown at Box 695B. This sending step may be done by the user "clicking" on a return key or other symbol.

The above descriptions are not intended to be limiting of scope of the inventions. For example, the present disclosure is not limited to a mouthpiece 110 having the configuration shown in FIGS. 2A through 2C; other configurations may be employed. The mouthpiece may only have, for instance, two cells placed in side-by-side relation. The mouthpiece 110 may have a handle (not shown).

In another arrangement, the mouthpiece does not use cells, tubes and pressure sensors, but instead operates on a system where electrical signals are sent directly from the mouthpiece. The mouthpiece may be arranged in a matrix, with pressure sensors being embedded directly into the mouthpiece within cells defined by the matrix. The pressure sensors may be tactile pressure sensors that detect pressure applied by the patient's tongue as the patient moves his or her tongue across the bottom surface of the bulb. The sensor may measure duration of pressure, direction of pressure, magnitude of pressure, or combinations thereof, at various cell locations.

Each pressure sensor may have its own signature signal. The signature signals are in electrical communication with a first interface. The first interface accumulates pressure data from the various signature signals. This data is then used to create the pressure profile.

In this arrangement, the first interface sends the signature signal data via a communications path. Preferably, the communications path is a wireless communications path directed to a second interface. Thus, as pressure is sensed by a sensor (not shown) in the mouthpiece, the sensor sends a signal to the first interface, which is then communicated to the second interface.

Various types of sensors may be used. For example, a tactile pressure sensor may be used that relies upon resistive-based technology. In this instance the sensor acts as a variable resistor in an electrical circuit. In this application, a small deflection of a matrix in the mouthpiece causes implanted resistors to exhibit a change in ohmic value. The sensor converts this change into a voltage or other electrical signal that is interpreted as a continuous and linear pressure reading. When tactile pressure sensors are unloaded, their resistance is very high. When force is applied, their resistance decreases.

Additional sensing means may be incorporated into each cell in order to sense direction of pressure. In addition, a clock may be associated with each signature signal to measure duration of a detected signal.

Other pressure-sensitive electrical arrangements may be employed. In this respect, the embodiment is not limited by the type of sensor utilized within the cells. For example, a piezo-electric material may be used.

A processor (not shown) is communicably connected with the second interface, such as through a wireless communications system. The processor processes the signature signals to translate location of sensed pressure to a location of an object within a display. The processor may also process the signature signals to translate magnitude of sensed pressure, direction of sensed pressure relative to pressure sensed by at least one other sensor, and the duration of sensed pressure. The processor may manipulate an object within a display, relative to obstacles.

While it will be apparent that the inventions herein described are well calculated to achieve the benefits and advantages set forth above, it will be appreciated that the inventions are susceptible to modification, variation and change without departing from the spirit thereof.

I claim:

1. A head set for facilitating movement of an object through lingual manipulation, the head set comprising:
   a head piece;
   an articulating arm extending from the head piece and having a distal end;

an elastomeric mouthpiece comprising a bulb, the bulb being connected proximate the distal end of the articulating arm, and the bulb having a plurality of fluid-containing cells embedded therein configured to respond to pressure applied by the tongue of an individual when the mouthpiece is in a mouth of the user;

a plurality of tubes, each tube having a proximal end and a distal end, with the distal end of each of the tubes being in substantially sealed fluid communication with a corresponding cell, and the proximal end being in substantially sealed fluid communication with a respective transducer wherein each transducer converts changes in pressure within the cells to electrical signals.

2. The head set of claim 1, further comprising:
a processor for processing the electrical signals, wherein the electrical signals are modulated to generate a pressure profile from the cells, the pressure profile representing a magnitude of pressure within cells, a direction of pressure, a duration of pressure, or combinations thereof.

3. The head set of claim 2, further comprising:
said transducers being mechanically supported by the head set.

4. The head set of claim 2, wherein the transducers and the processor are not mechanically supported by the head set but are tethered to the head set through the plurality of tubes.

5. The head set of claim 2, wherein:
each cell and each tube contains (i) a compressible fluid, (ii) a non-toxic incompressible fluid, or (iii) a combination thereof.

6. The head set of claim 2, wherein:
each cell and each tube contains a compressible fluid; and
the compressible fluid comprises air, oxygen, carbon dioxide, nitrogen, or combinations thereof.

7. The head set of claim 2, wherein:
each cell and each tube contains a non-toxic incompressible fluid; and
the incompressible fluid comprises water.

8. The head set of claim 2, wherein the mouthpiece is fabricated from polyisoprene rubber, silicone, chloroprene rubber, neoprene, styrene butadiene rubber, acrylonitrile butadiene rubber, ethylene propylene diene methylene, polyvinylchloride, polyethylene, polyurethane, urethane-coated nylon, ethyl vinyl acetate, and combinations thereof.

9. The head set of claim 2, wherein the bulb comprises at least three outer cells disposed radially around a centerpoint.

10. The head set of claim 9, wherein the centerpoint defines a separate central cell in fluid communication with one of the plurality of tubes.

11. The head set of claim 2, wherein each of the plurality of tubes has an inner diameter of about 0.05 inches to 0.5 inches.

12. The head set of claim 2, wherein each of the plurality of tubes resides substantially at ambient pressure.

13. The head set of claim 2, wherein each of the plurality of tubes is pre-loaded at a pressure of about 15 psi to 25 psi.

14. The head set of claim 2, wherein each of the plurality of transducers is a pressure sensor having a diaphragm that is sensitive to changes in pressure within a tube.

15. The head set of claim 2, wherein the signal processor receives electrical signals from each of the plurality of transducers and processes those signals such that:
each electrical signal represents a pressure reading from a corresponding cell; and
electrical signals from one or more corresponding cells are averaged over a specified period of time to produce the pressure profile, the pressure profile having a peak indicative of location at which pressure is being generated within the one or more cells during the specified period of time.

16. The head set of claim 2, wherein the head piece comprises a pair of opposing head rests, with at least one of the head rests being adjustable relative to the head piece.

17. The head set of claim 2, wherein the articulating arm comprises:
a first arm portion extending from one of the opposing head rests, and comprising a pivot point away from the head rest; and
a second arm portion connected to the pivot point, and having the distal end away from the pivot point.

18. The head set of claim 2, wherein the head piece is configured such that the first arm portion may be selectively connected to either of the opposing head rests.

19. The head set of claim 2, wherein each of the plurality of tubes comprises more than one tubular body operatively connected through a manifold to form individual, fluidically sealed channels.

20. The head set of claim 2, wherein:
the processor is in electrical communication with (i) a motor for moving an object, (ii) a switch for changing an electrical state of an appliance, or (iii) a cursor on a display; and
a magnitude of each electrical signal is recorded as part of the pressure profile over the specified period of time.

21. The head set of claim 20, wherein the electrical signal is a voltage signal.

22. The head set of claim 20, wherein:
the processor is in electrical communication with a motor for moving an object; and
the object is a bed, a wheelchair, or a door.

23. The head set of claim 20, wherein:
the processor is in electrical communication with a switch for changing an electrical state of an appliance; and
the switch controls a light fixture, a television, or a thermostat.

24. The head set of claim 23, wherein the bulb comprises at least three outer cells disposed radially around a centerpoint.

25. The head set of claim 24, wherein an application of pressure by a user on the centerpoint for a specified period of time and at a specified magnitude causes a location of the object to be reset to a beginning point on the display.

26. The intra-oral system of claim 23, wherein:
the processor is in electrical communication with a cursor on a display
an application of pressure by the user on a designated outer cell for a specified period of time and at a specified magnitude causes a location of the cursor to be moved to a corresponding location on the display.

27. A method for moving a cursor on a display using lingual manipulation, comprising:
providing a head set for a user, the head set comprising:
a head piece;
an articulating arm extending from the head piece and having a distal end;
an elastomeric mouthpiece comprising a bulb, the bulb being connected proximate the distal end of the articulating arm, and the bulb having a plurality of fluid-containing cells embedded therein for receiving pressure applied by the tongue of an individual; and
a plurality of tubes, each tube having a proximal end and a distal end, with the distal end of each of the tubes being in substantially sealed fluid communication with a corresponding cell, and the proximal end being in substantially sealed fluid communication with a respective transducer wherein each transducer converts changes in pressure within the cells to electrical signals;

providing a processor for processing the electrical signals, wherein the electrical signals are modulated to generate a pressure profile from the cells, the pressure profile representing a magnitude of pressure within the cells, a direction of pressure, a duration of pressure, or combinations thereof;

placing the plurality of tubes in fluid communication with the corresponding plurality of transducers;

placing the processor in operative electrical communication with a cursor on a display so that a user may cause the cursor on the display to move in accordance with the pressure profile using lingual manipulation.

28. The method of claim 27, wherein the transducers are mechanically supported by the head set.

29. The method of claim 27, wherein the transducers reside in an operational box, and are in fluid communication with the plurality of tubes by means of a manifold.

30. The method of claim 27, wherein the head piece comprises a pair of opposing head rests, with at least one of the head rests being adjustable relative to the head piece.

31. The method of claim 27, wherein the articulating arm comprises:
a first arm portion extending from one of the opposing head rests, and comprising a pivot point away from the head rest; and
a second arm portion connected to the pivot point, and having the distal end away from the pivot point.

32. The method of claim 27, wherein the head piece is configured such that the first arm portion may be selectively connected to either of the opposing head rests.

33. The method of claim 27, wherein:
each cell and each tube contains (i) a compressible fluid, (ii) a non-toxic incompressible fluid, or (iii) a combination thereof.

34. The method of claim 27, wherein the compressible fluid comprises air, oxygen, carbon dioxide, nitrogen, or combinations thereof.

35. The method of claim 34, wherein the incompressible fluid comprises water.

36. The method of claim 27, wherein the mouthpiece is fabricated from polyisoprene rubber, silicone, chloroprene rubber, neoprene, styrene butadiene rubber, acrylonitrile butadiene rubber, ethylene propylene diene methylene, polyvinylchloride, polyethylene, polyurethane, urethane-coated nylon, ethyl vinyl acetate, and combinations thereof.

37. The method of claim 27, wherein the signal processor receives electrical signals from each of the plurality of transducers and processes those signals such that:
each electrical signal represents a pressure reading from a corresponding cell; and
electrical signals from one or more corresponding cells are averaged over a specified period of time to produce the pressure profile, the pressure profile having a peak indicative of location at which pressure is being generated within the one or more cells during the specified period of time.

38. The method of claim 37, further comprising:
providing one or more symbols on the display; and
selecting a symbol to actuate a mechanical device or an electrical appliance.

39. The method of claim 38, wherein the processor is configured such that the user may click on a symbol on the display by applying pressure on a centerpoint of the mouthpiece for a specified period of time and at a specified magnitude.

40. The method of claim 38, wherein the symbol on the display comprises a picture, one or more alphanumeric characters, an arrow, or a geometric figure.

41. The method of claim 38, wherein:
the processor is in electrical communication with a motor for moving an object; and
one of the one or more symbols on the display corresponds to the object.

42. The method of claim 41, wherein the object is a bed, a wheelchair, or a door.

43. The method of claim 38, wherein:
the processor is in electrical communication with a switch for changing an electrical state of an appliance; and
one of the one or more symbols on the display corresponds to the appliance.

44. The method of claim 43, wherein the appliance is a light fixture, a television, or a thermostat.

45. The method of claim 41, wherein the processor is configured such that the user may click on a symbol on the display by applying pressure on a centerpoint of the mouthpiece for a specified period of time and at a specified magnitude.

46. The method of claim 38, wherein:
a magnitude of each electrical signal is recorded as part of the pressure profile over the specified period of time.

47. The method of claim 38, wherein each of the plurality of transducers is a pressure sensor having a diaphragm that is sensitive to changes in pressure within a tube.

48. The method of claim 38, wherein the bulb comprises at least three outer cells disposed radially around a centerpoint.

49. The method of claim 48, wherein the centerpoint defines a separate cell in fluid communication with one of the plurality of tubes.

50. The method of claim 27, wherein each of the plurality of tubes has an inner diameter of about 0.05 inches to 0.5 inches.

51. The method of claim 27, wherein each of the plurality of tubes resides substantially at ambient pressure.

52. The method of claim 27, wherein each of the plurality of tubes is pre-loaded at a pressure of about 15 psi to 25 psi.

53. The method of claim 38, wherein an application of pressure by a patient on a designated outer cell for a specified period of time and at a specified magnitude causes a location of the cursor to be moved to a corresponding location or a corresponding symbol on the display.

54. The method of claim 38, wherein one or more symbols on the display comprises a keyboard such that the user may select a series of characters on the keyboard using their tongue to composing a textual message.

55. The method of claim 54, further comprising:
providing a "send" symbol on the display that, when selected by the user, the textual message is sent through a wireless communications system.

56. A method of typing characters on a virtual keyboard using lingual musculature, comprising:
wearing a head set on a head, the head set comprising:
a head piece;
an articulating arm extending from the head piece and having a distal end;
an elastomeric mouthpiece comprising a bulb, the bulb being connected proximate the distal end of the articulating arm, and the bulb having a plurality of fluid-containing cells embedded therein for receiving pressure applied by the tongue of an individual; and a plurality of tubes, each tube having a proximal end and a distal end, with the proximal end of each of the tubes being in substantially sealed fluid communication with a corresponding plurality of transducers for converting changes in pressure within the cells to electrical signals, and with the distal end of each of the tubes being in substantially sealed fluid communication with a corresponding cell; and placing the mouthpiece in one's mouth;

moving one's tongue across a bottom surface of the mouthpiece;

applying pressure to cells of the mouthpiece in order to move a cursor on a display, the display having a digital keyboard and the cursor moving across the digital keyboard in accordance with a pressure profile, the pressure profile representing a magnitude of pressure within the cells, a direction of pressure, a duration of pressure, or combinations thereof;

using the cursor to select characters on the digital keyboard; and clicking on selected characters on the digital keyboard using lingual musculature on the mouthpiece in order to compose a textual message.

57. The method of claim 56, wherein:

applying pressure to the cells causes changes in air pressure within the plurality of tubes, such changes being sensed by each of the plurality of transducers and converted to an electrical signal;

the transducers are in operative electrical communication with a processor which processes the electrical signals in order to generate the pressure profile; and the processor is in operative electrical communication with the display for causing the cursor to move across the digital keyboard.

58. The method of claim 56, wherein each of the plurality of transducers is a pressure sensor having a diaphragm that is sensitive to changes in pressure within a tube.

59. The method of claim 57, further comprising:

sending the textual message through a wireless communications system.

60. The method of claim 57, wherein the signal processor receives electrical signals from each of the plurality of transducers and processes those signals such that:

each electrical signal represents a pressure reading from a corresponding cell; and electrical signals from one or more corresponding cells are averaged over a specified period of time to produce the pressure profile, the pressure profile having a peak indicative of location at which pressure is being generated within the one or more cells during the specified period of time.

* * * * *